United States Patent
Tümpner (10) Patent No.: US 9,353,346 B2
(45) Date of Patent: May 31, 2016

(54) INCUBATOR DEVICE AND METHOD (75) Inventor: Jürgen Tümpner, Münster (DE)

(73) Assignee: OLYMPUS SOFT IMAGING SOLUTIONS GMBH, Munster (DE)

(*) Notice: Subject to any disclaimer, the term of this patent is extended or adjusted under 35 U.S.C. 154(b) by 429 days.

(21) Appl. No.: 13/126,832

(22) PCT Filed: Oct. 29, 2009

(86) PCT No.: PCT/EP2009/064311
§ 371 (c)(1),
(2), (4) Date: Jul. 14, 2011

(87) PCT Pub. No.: WO2010/049498
PCT Pub. Date: May 6, 2010

(65) Prior Publication Data
US 2011/0263010 A1 Oct. 27, 2011

(30) Foreign Application Priority Data
Oct. 30, 2008 (DE) .......... 10 2008 053 942

(51) Int. Cl.
C12M 1/00 (2006.01)
C12N 1/04 (2006.01)
C12M 1/26 (2006.01)

(52) U.S. Cl.
CPC .............. *C12M 41/14* (2013.01); *C12M 33/00* (2013.01)

(58) Field of Classification Search
USPC .......................................... 435/283.1–309.4
See application file for complete search history.

(56) References Cited

U.S. PATENT DOCUMENTS

| 3,929,584 A | 12/1975 | Mansfield |
| 4,426,923 A | 1/1984 | Ohata |
| 4,892,830 A | 1/1990 | Findley et al. |

(Continued)

FOREIGN PATENT DOCUMENTS

| DE | 873 892 | 4/1953 |
| DE | 253 432 A1 | 1/1988 |

(Continued)

OTHER PUBLICATIONS

International Search Report dated Jun. 28, 2010 issued in International Appln. No. PCT/EP2009/064311.

(Continued)

*Primary Examiner* — Nathan Bowers
*Assistant Examiner* — Lydia Edwards
(74) *Attorney, Agent, or Firm* — Holtz, Holtz & Volek PC (57) ABSTRACT The invention provides an incubation device, comprising an incubator chamber (12), a specimen carrier (15), which is designed to accommodate a specimen (14) and position it in the interior of the incubator chamber (12) at a specimen position (P), a heating arrangement (38, 40) with at least one heating element (38, 40), which is arranged inside the incubator chamber (12) and releases heat to the interior of the incubator chamber (12), a humidifier (16) for producing a humidifying fluid, and a passage opening (30) arranged between the humidifier (16) and the interior of the incubator chamber (12), through which the humidifying fluid may pass into the interior of the incubator chamber (12), wherein the interior of the incubator chamber (12) is substantially free of directed fluid flow at least at the specimen position (P).

11 Claims, 2 Drawing Sheets

(56) References Cited

U.S. PATENT DOCUMENTS

| | | |
|---|---|---|
| 5,851,790 A | 12/1998 | Walker et al. |
| 5,976,871 A | 11/1999 | Walker et al. |
| 7,765,868 B2 | 8/2010 | Pirsch et al. |
| 7,867,762 B2 | 1/2011 | Stahl et al. |
| 2005/0282268 A1 | 12/2005 | Kagayama |
| 2011/0107788 A1 | 5/2011 | Stahl et al. |

FOREIGN PATENT DOCUMENTS

| | | |
|---|---|---|
| DE | 202 14 480 U1 | 1/2003 |
| DE | 696 34 765 T2 | 11/2005 |
| DE | 10 2005 023 855 A1 | 1/2006 |
| DE | 101 32 761 B4 | 2/2006 |
| DE | 20 2006 003844 U1 | 5/2006 |
| DE | 10 2005 018142 A1 | 10/2006 |
| DE | 10 2005 033 927 A1 | 6/2007 |
| DE | 10 2006 022652 A1 | 11/2007 |
| EP | 1 552 888 A2 | 7/2005 |
| GB | 812 417 A | 4/1959 |
| WO | WO 88/075 74 A1 | 10/1988 |
| WO | WO 01/30 962 | 5/2001 |
| WO | WO 2005/030 394 A1 | 4/2005 |

OTHER PUBLICATIONS

German Office Action dated Mar. 18, 2009 (and English translation thereof) in counterpart German Application No. 10 2008 053 942.2-52.
Zeiss Manual Axiovert 200 + 200 M (in English and German).
Leica Manual DM IRE 2, DM IRB + AS TP (in English and German).
Article from in Vivo Scientific (in English) (htto://www.invivoscientific.com/Incubators.htm).
Manual Axiovert 100/135 (in English and German).
Stephen Baron et al.: Konstruktion and Etablierung einer Klimakammer fur die Untersuchung der embryonalen Herzentwicklung (no English translation available).

INCUBATOR DEVICE AND METHOD

This application is a U.S. National Phase Application under 35 USC 371 of International Application PCT/EP2009/064311 filed Oct. 29, 2009.

The present invention comprises an incubator device with an incubator chamber and a specimen carrier arranged therein for accommodating a specimen, and an incubation method.

Incubator devices and incubation methods of the stated type are known in the prior art and are used in industry and research wherever biological or medical materials or other substances or objects (hereinafter known generally as "specimens") need to be exposed to a defined climate for a specific period. For example, for the examination of living cells, for instance using a microscope, the provision of ambient conditions adapted to the specimen is crucial for meaningful examination results and accordingly constitutes a significant technological challenge when performing such measurements or examinations. Temperature and humidity have a major influence on the behaviour of biological specimens. The climate defined by these parameters has to be kept as constant as possible for the duration of the examination of the specimen, in order on the one hand not to change the specimen in itself and on the other hand as far as possible to reduce interaction of the climate with the measuring or examining instruments used.

An incubator device for establishing such a defined climate is known from WO 2005/030394 A1. This device is of sufficient size to enclose part of a microscope assembly and to ensure sufficient space for easy handling of the specimen within the incubator chamber. A desired internal temperature is achieved by introducing a conditioned gas into the interior of the incubation chamber, the temperature-controlled gas jet being oriented in the direction of the specimen holder, such that the specimen may be heated or cooled in the gas jet.

The relatively large incubator chamber of the incubator device known from WO 2005/030394 A1 has the advantage that various additional devices, for example for in-situ preparation of specimens or for additional measurements or examinations, may be accommodated therein and thus a versatile incubator device is provided. A main disadvantage of this device and other relatively large incubator chambers is the difficulty of achieving homogeneous temperature distribution or maintaining a reliable, defined temperature at the site of the specimen. To control the temperature of the relatively large chamber volume, a sufficiently high air flow rate is necessary, to which the specimen is also exposed and which leads to undefined, relatively significant temperature gradients in the interior of the incubator chamber. The formation of temperature gradients is further promoted by the combination of a small gas inlet zone for the humidifying gas and a relatively large interior volume. Finally, it cannot be ruled out that specimen parts may be located at different positions in the incubator chamber under different climatic conditions or the climate in the incubator chamber may change at the specimen position in the course of measurement, whereby the meaningfulness and accuracy of the measurements or examinations performed are significantly impaired.

An incubator device known from DE 10 2005 033 927 A1 uses an outer incubator chamber, in which an inner incubator chamber is accommodated, wherein a specimen holder is arranged in the inner incubator chamber to accommodate a specimen to be examined. The inner incubator chamber is in contact with a heatable intermediate plate arranged outside the incubator chamber, such that heat may be introduced by heat conduction through the specimen holder into the specimen, in order to heat the specimen.

Although a spatially and temporally constant climate may be more simply established or maintained using a smaller incubator chamber, such as the incubator chamber known from DE 10 2005 033 927 A1, such incubator devices exhibit only extremely limited flexibility with regard to the performance of examinations or measurements, since insufficient space is available for additional tools or for handling (preparation) of the specimen. Often smaller incubator devices are set up for one-off preparation of specimens before the start of examinations and do not allow any further access to the specimen once the incubator chamber has been closed.

Against this background it is the object of the present invention to provide an incubator device and an incubation method with which a specimen may be exposed for a given period of time to a definable climate constant over the specimen surface, while a minimum of flexibility remains with regard to the intended purpose and operation of the incubator device.

According to a first aspect, this object is achieved by an incubator device, comprising an incubator chamber, a specimen carrier, which is designed to accommodate a specimen and position it in the interior of the incubator chamber at a specimen position, a heating arrangement with at least one heating element, which is arranged inside the incubator chamber and releases heat to the interior of the incubator chamber, a humidifier for producing a humidifying fluid, and a passage opening arranged between the humidifier and the interior of the incubator chamber, through which the humidifying fluid may pass into the interior of the incubator chamber, wherein the interior of the incubator chamber is substantially free of directed fluid flow at least at the specimen position.

For the purposes of this disclosure, a fluid, in particular a humidifying fluid, should be understood to be a gas or any mixture of gas and liquid. A humidifying fluid may be a gaseous medium with a humidity in a desired range, but may also take the form of a mist, a vapour or an aerosol with a plurality of liquid particles in the micrometre range distributed finely therein. The humidifying fluid may furthermore also exhibit a lower humidity than the surrounding environment, in order in this way to reduce the humidity of the specimen environment.

The invention is based on the knowledge, gained in numerous experiments carried out by the inventor, that the time profile of the temperature and humidity at the specimen position and a gradient of the temperature and humidity over the surface of the specimen lead to impairment of the measuring and examination results due to the gas flows inevitably generated in the interior of the incubator chamber by the conditioning apparatuses of conventional incubator devices. With the arrangement according to the invention, on the other hand, it is proposed to influence both the humidity and temperature of the specimen substantially without any fluid flow at the site of the specimen.

Closely associated with this inventive concept are two important principles which have been put into practice in the incubator device according to the invention: on the one hand, by arranging a heating arrangement with at least one heating element inside the incubator chamber, which releases heat to the interior of the incubator chamber, temperature control of the specimen or of the interior of the incubator chamber may be achieved wholly without the provision of a heat transfer gas or the like to be passed through the interior. The at least one heating element radiates its heat directly into the interior of the incubator chamber or onto the specimen, i.e. the active heating surface of the heating element is uncovered towards the interior, such that the specimen temperature may be influ- 
enced quickly and accurately, without using a fluid flow which impairs the constant nature of the climate.

The second important principle is the separation of temperature control and humidity control by providing a humidifier separate from the heating arrangement. The humidifier also operates in accordance with the principle according to the invention of as far as possible preventing fluid flows at the specimen position in the interior of the incubator chamber, but in any case building up a substantially completely flow-free environment at the site of the specimen. This is achieved in that the humidifier is separated from the incubator chamber by way of a passage opening and the humidifying fluid passes through this passage opening into the incubator chamber, but quickly loses its directed flow after entry into the incubator chamber, such that at least the environment directly surrounding the specimen remains virtually completely free of flow.

A flow-free state in the specimen's surrounding environment means, for the purposes of the present invention, a state in which heat, humidity or other parameters influencing the climate at the specimen position are not significantly altered by a flow directed in any way attributable to introduction of the humidifying fluid. A distinction should be drawn between this and any convection flow in the interior of the incubator chamber, which is caused for example by the heat generated by the heating elements. Other slow flows, such as for example diffusion due to the intrinsic thermal motion of the gas or liquid particles in the incubator chamber and Brownian motion, may be used according to the invention to distribute the humidifying medium in the incubator chamber and also to feed it to the specimen without generating a flow at the specimen position which destabilises the specimen climate. Such convection or diffusion flows lead with significantly lower flow velocities to natural gas circulation in the interior of the incubator chamber, but are so weak and slow that they barely impair the precision and constancy over time of the climate at the specimen position.

Preferably, the humidifying fluid enters the interior of the incubator chamber at the passage opening with directed flow, wherein the velocity at which the humidifying fluid passes through the passage opening is adjusted such that the humidifying fluid flows with directed flow upstream of and in the passage opening and after passage through the passage opening, in the interior of the incubator chamber, the directed flow of the humidifying fluid drops substantially to zero within a short transition zone. The velocity range for fulfilling this condition depends on the geometry and operating data of the incubator chamber. A person skilled in the art can easily establish a precise value by simple measurement on an actual incubator chamber, for example by using a flow sensor at the site of the specimen or by a coloured humidifying fluid in combination with modification of the velocity at which the humidifying fluid passes into the incubator chamber.

In one embodiment of the invention provision is made for the specimen carrier to be designed to position a specimen in the interior of the incubator chamber at a specimen position which is at a predetermined distance from the passage opening, wherein length of the transition zone in the passage direction of the passage opening is between roughly 0 and roughly 1/4, preferably between roughly 1/100 and roughly 1/10 of the predetermined distance. Investigations by the inventor have shown that in the range between roughly 0 and roughly 1/10 of the predetermined distance a distinct improvement arises in the temporal and spatial constancy of the climate at the specimen position. Particularly good results for specific quality requirements may be achieved in the range between roughly 1/100 and roughly 1/10, the passage flow being so low for values below 1/100 that reliable and continuous passage of the humidifying fluid into the incubator chamber is jeopardised, while for values over 1/10 an increasing effect of the flow velocity on the specimen climate was noted.

However, it was also possible to establish, irrespective of the precise size of the incubator chamber, that the length of the transition zone in the passage direction of the passage opening should advantageously be between roughly 0 cm and roughly 10 cm, particularly good results being achieved for more stringent climate constancy requirements with a transition zone length range of between roughly 1 cm and roughly 3 cm. Below roughly 1 cm there is a risk of failure of continuous feed of humidifying fluid, while for values over roughly 3 cm the flow velocity has a noticeable influence on the specimen climate.

The humidifier is preferably an aerosol apparatus, which generates a humidifying fluid on the basis of a liquid aerosol. An aerosol apparatus is distinguished relative to alternative conventional methods of producing a humidifying fluid (e.g. vaporisation of sacrificial liquid) in that the liquid is introduced rapidly and directly in the form of an aerosol into the surrounding gas, to humidify the latter. The aerosol vaporises relatively quickly due to the thermal energy of the surrounding gas. This vaporisation may take place immediately after production of the aerosol microspheres, i.e. prior to passage into the incubator chamber, and/or not until inside the incubator chamber.

The aerosol apparatus may furthermore comprise a piezo oscillating element, for generating the liquid aerosol from a service liquid. Such a piezo oscillating element may be actuated particularly easily and quickly and very quickly generates aerosol particles in the range of a few micrometres from the service liquid due to its high frequency oscillation. Humidity adjustment using such an aerosol apparatus is extremely quick and may be precisely adjusted or switched on or off. At the same time, it is responsible solely for humidity adjustment and thus does not affect the temperature of the specimen. Humidity adjustment and temperature control of the specimen are decoupled according to the invention.

Preferably, the incubator device additionally comprises a fluid drive means for producing a directed flow of the humidifying fluid at a predetermined velocity towards the passage opening. The velocity conferred on the humidifying fluid by the fluid drive means is selected according to the above-stated criteria such that in the interior of the incubator chamber, but at least in the immediate vicinity of the specimen, there is no longer any humidifying fluid flow present which goes beyond the slow convection flow.

In a further embodiment the incubator device comprises a gas outlet opening, which is provided separately of the passage opening, such that gas may leave the incubator chamber through the gas outlet opening. In this way an internal pressure in the incubator chamber may be influenced and for example constant pressure conditions achieved in the interior of the incubator chamber. The gas outlet opening may advantageously be connected to the passage opening or to the humidifier via a circulation channel, such that gas leaving the gas outlet opening may be recirculated to the passage opening or to the humidifier. The fluid drive means may then be arranged in the circulation channel or between aerosol apparatus and passage opening, such that it causes closed, continuous gas circulation. If the fluid drive means comprises a suction means, for drawing fluid out of the incubator chamber into the circulation channel, a defined flow velocity may be achieved with simple, per se known means.

The flow velocities generated by the fluid drive means are here selected according to the invention such that they ensure continuous passage of the humidifying fluid into the incubator chamber but substantially do not affect the flow conditions in the interior of the incubator chamber. After entry of the humidifying fluid into the incubator chamber the humidifying fluid is distributed in the incubator chamber virtually solely on the basis of convection flow, Brownian particle motion etc. The inventors have established that these virtually random, undirected or very slow flow motions alone in the interior of the incubator chamber are sufficiently or even surprisingly better suited to reliably producing the desired humidity at a specimen position and keeping it constant. In particular, the inventors have ignored the prejudice within specialist circles that a constant climate at the specimen position would require a constant, directed flow of conditioning gas over the specimen.

In a further preferred embodiment of the invention the heating arrangement is constructed substantially symmetrically relative to a vertical axis through the specimen position and/or exhibits heat release characteristics which are symmetrical relative to this axis. The symmetrical configuration of the heating arrangement brings about a substantially only vertical temperature gradient within the incubator chamber, which results in the temperature of the specimen being constant at least over the specimen surface. For the purposes of the present invention terms such as horizontal, vertical, up, down, sideways and the like are intended to relate to a normal operating situation of the incubator chamber and to a flat shape and orientation of the specimen in a horizontal plane. These details should not be interpreted as being limiting and may also be straightforwardly applied analogously to other orientations or geometries of the specimen or other geometries and orientations of the incubator chamber.

In one particularly preferred configuration the at least one heating element is plate-shaped, such that it has a relatively large heat release surface. In this case, in particular a planar heating element is proposed, e.g. a low temperature planar heating element, such that maximally homogeneous temperature distribution may be achieved in the heat radiation field of the heating element.

The main heat radiation direction of the at least one heating element preferably points towards the specimen position. In this way, good homogeneous heating of the specimen may be achieved substantially by thermal radiation, which enables rapid and precise temperature control. A particularly effective arrangement has proven to be an embodiment in which a plurality of upper heating plates are arranged above a specimen plane and substantially symmetrically relative to a vertical axis extending through the specimen position and/or a plurality of lower heating plates are arranged below the specimen plane and substantially symmetrically relative to the vertical axis. In this arrangement a relatively large area surrounding the specimen is exposed to a substantially constant temperature field, a temperature gradient occurring at most in a vertical direction.

In embodiments of the invention described above, an incubator device with a substantially flow-free specimen environment was realised primarily through selection of a suitable passage velocity of the humidifying fluid into the incubator chamber. In further embodiments of the invention it is however likewise feasible, in addition or as an alternative to limiting passage velocity, to take measures which prevent the directed flow of the humidifying fluid from reaching the specimen environment. Such a measure may take the form of provision of a humidifying fluid deflecting face, which is arranged downstream of the passage opening in the passage direction of the humidifying fluid, i.e. in the interior of the incubator chamber, such that humidifying fluid which has entered the incubator chamber impinges on the humidifying fluid deflecting face. It would moreover be conceivable to position the passage opening at such a position within the incubator chamber that there is no direct connection between passage opening and specimen within the incubator chamber. In this way, the directed flow of the humidifying fluid is unable, at least directly, to reach the specimen position, such that even at relatively high passage velocities of the humidifying fluid it may be ensured that at least the immediate specimen environment is free of directed flow. Other means effecting break-up of the flow of the humidifying fluid within the incubator chamber may also be used.

In relation to such additional or alternative measures for reducing the directed flow of humidifying fluids at the specimen position, according to a second aspect of the invention an incubator device is provided to achieve the above-stated object of the invention which comprises an incubator chamber, a specimen carrier, which is designed to accommodate a specimen and position it in the interior of the incubator chamber at a specimen position, a heating arrangement with at least one heating element, which is arranged inside the incubator chamber and releases heat to the interior of the incubator chamber, a humidifier for producing a humidifying fluid, and a passage opening arranged between the humidifier and the interior of the incubator chamber, through which the humidifying fluid passes with directed flow into the interior of the incubator chamber in a passage flow direction, wherein the passage flow direction extends in a direction away from the specimen position.

Thus, according to the second aspect of the invention the humidifying fluid is intended to exhibit a flow direction on passage into the incubator chamber which leads away from the specimen position. A direction which leads away from the specimen position is understood for the purposes of the present invention to mean any direction of flow in which the flowing particles of the humidifying fluid at least do not approach the specimen position. This means that an angle of at least around 90° should be formed between a line connecting the passage opening and the specimen position and the passage flow direction.

By means of a passage opening with such a passage flow direction, the humidifying fluid is not sent in the direction of the specimen after entering the incubator chamber but rather is sent in another direction, such that particles of the humidifying fluid flowing in a directed manner cannot reach the specimen position or are able to reach it only after reflection at another element in the interior of the incubator chamber. Directed flow at the specimen site may in this way be prevented or reduced to the extent that substantially only undirected flow conditions resulting from natural (thermal) convection streams and diffusion are present at the specimen position.

According to a third aspect, the object of the invention is achieved by an incubator device comprising an incubator chamber, a specimen carrier, which is designed to accommodate a specimen and position it in the interior of the incubator chamber at a specimen position, a heating arrangement with at least one heating element, which is arranged inside the incubator chamber and releases heat to the interior of the incubator chamber, a humidifier for producing a humidifying fluid, and a passage opening arranged between the humidifier and the interior of the incubator chamber, through which the humidifying fluid passes with directed flow into the interior of the incubator chamber in a passage flow direction, wherein the passage flow direction is directed against a humidifying fluid deflecting face, at which the humidifying fluid is deflected.

As with the incubator device of the above-stated second aspect of the invention, in the incubator device of the third aspect of the invention too direct flow of the humidifying fluid to the specimen position after passage through is prevented, wherein according to the third aspect a humidifying fluid deflecting face is used for this purpose at which the humidifying fluid is deflected, preferably into a direction away from the specimen position. Adjustment of the direction of flow of the humidifying fluid does not then have to take place actually at the passage opening but rather may be provided by the humidifying fluid deflecting face, which may also be retrofitted downstream of a passage opening.

Advantageously, the features of the incubator devices of the second and third aspects of the invention may be combined together, by combining a passage opening already pointing away from the specimen with a humidifying fluid deflecting face, in order further to extend the path of the humidifying fluid to the specimen position or to prevent humidifying fluid from colliding with particularly elements in the interior of the incubator chamber. In addition, incubator devices of the second or third aspect may in each case be further developed, alone or in combination with one another, by one or more of the features explained in connection with the first aspect of the invention, in order to achieve the effects stated above at the corresponding point. For instance, it is however also preferred in particular in the case of incubator devices of the second and/or third aspect of the invention for the directed flow of humidifying fluid to be substantially completely broken up at the specimen site, such that only natural convection streams resulting from the temperature adjustments of the heating means or undirected diffusion streams are present at the specimen position.

In a preferred embodiment of the incubator device of the third aspect of the invention, the humidifying fluid deflecting face may be formed on the heating arrangement. In this way, not only is a saving made in components due to the dual function of the heating arrangement as a heat source and as a humidifying fluid deflecting face, but deflection of the humidifying fluid at the heating arrangement further offers the advantage that the humidifying fluid is not condensed at the heated deflecting face and thus the input of humidity into the interior of the incubator chamber is not reduced. In addition, by avoiding condensation soiling of the humidifying fluid deflecting face is also avoided.

The passage opening may be arranged in a wall portion of the incubator chamber defining the interior of the incubator chamber, in order to ensure a simple construction of the device. In one embodiment of the invention, however, it is conceivable for the passage opening to be provided at a nozzle portion of a fluid line extending in the interior of the incubator chamber. Such a fluid line offers the possibility of positioning the passage opening simply at a desired position in the interior of the incubator chamber and/or of adjusting the passage flow direction of the passage opening by appropriate organisation of the line or appropriate configuration of the nozzle portion. Such a fluid line may furthermore branch in the interior of the incubator chamber, so that a plurality of passage openings may be arranged at different positions in the interior of the incubator chamber and thus the flow conditions in the incubator chamber may be further calmed. These advantages may be used for incubator devices according to all aspects of the invention.

The invention may be used with particular advantage if the incubation device comprises a microscope for observing and/or measuring the specimen, wherein the specimen carrier comprises or forms the specimen holder of the microscope and wherein at least the specimen carrier or substantially the entire microscope is accommodated inside the incubator chamber. As a result of the combination according to the invention of heating arrangement and humidifying arrangement, a spatially and temporally constant climate may also be maintained in a relatively large incubator chamber, such that the invention is particularly suitable for a microscope and at the same time provides sufficient space for handling the specimen in the incubator chamber or for additional measurements/examinations of the specimen in the specimen holder of the microscope.

According to a fourth aspect of the invention, the object of the invention is further achieved by an incubation method which comprises the following steps:
  accommodating a specimen in a specimen carrier in the interior of an incubator chamber at a specimen position,
  operating at least one heating element arranged in the interior of the incubator chamber, such that it releases heat to the interior of the incubator chamber,
  operating a humidifier, such that it produces a humidifying fluid, and
  moving the humidifying fluid to a passage opening, such that the humidifying fluid may pass through this into the interior of the incubator chamber, wherein the movement proceeds at a predetermined velocity, which is sufficiently low for the interior of the incubator chamber to be substantially free of directed fluid flow at least at the specimen position.

In the step of moving the humidifying fluid to the passage opening the velocity of movement of the humidifying fluid may be adjusted in accordance with the criteria mentioned above for the incubator device according to the invention, in order in particular to adjust the size of the transition zone between directed flow and break up of the directed flow.

With the incubation method according to the invention the effects and advantages are achieved which are achieved with the corresponding features of the above-described incubation device and were described above. The incubation method is preferably performed with an incubation device according to the invention of the above-described type.

The invention further extends to a method for microscopic examination and/or measurement of a specimen, comprising an incubation method of the above-stated type. As a result of the improved spatial and temporal constancy of the climate in the immediate vicinity of the specimen due to the incubation method according to the invention, the method for microscopic examination and/or measurement of a specimen achieves the advantage, according to the invention, that more reliable and meaningful examination/measurement results may be achieved.

For the actual size of the transition zone, the inventors have found a range of between roughly 0 cm and roughly 10 cm, preferably a range of between roughly 1 cm and roughly 3 cm to be particularly effective. In the preferred range of between roughly 1 cm and roughly 3 cm it is possible on the one hand to ensure reliable passage of the humidifying fluid into the incubator chamber and on the other hand reliably to prevent any directed flow at the specimen position due to the inflowing humidifying fluid.

Furthermore, the object of the invention is achieved by incubation methods according to a fifth and sixth aspect of the invention. These incubation methods achieve the effects and advantages which were described by the special features of the above-described incubator devices of the second or third aspects of the invention and they may preferably be performed using an incubator device according to the second or third aspects of the invention.

The invention is explained in greater detail below on the basis of preferred exemplary embodiments with reference to the attached drawings, in which.

Figure 1:
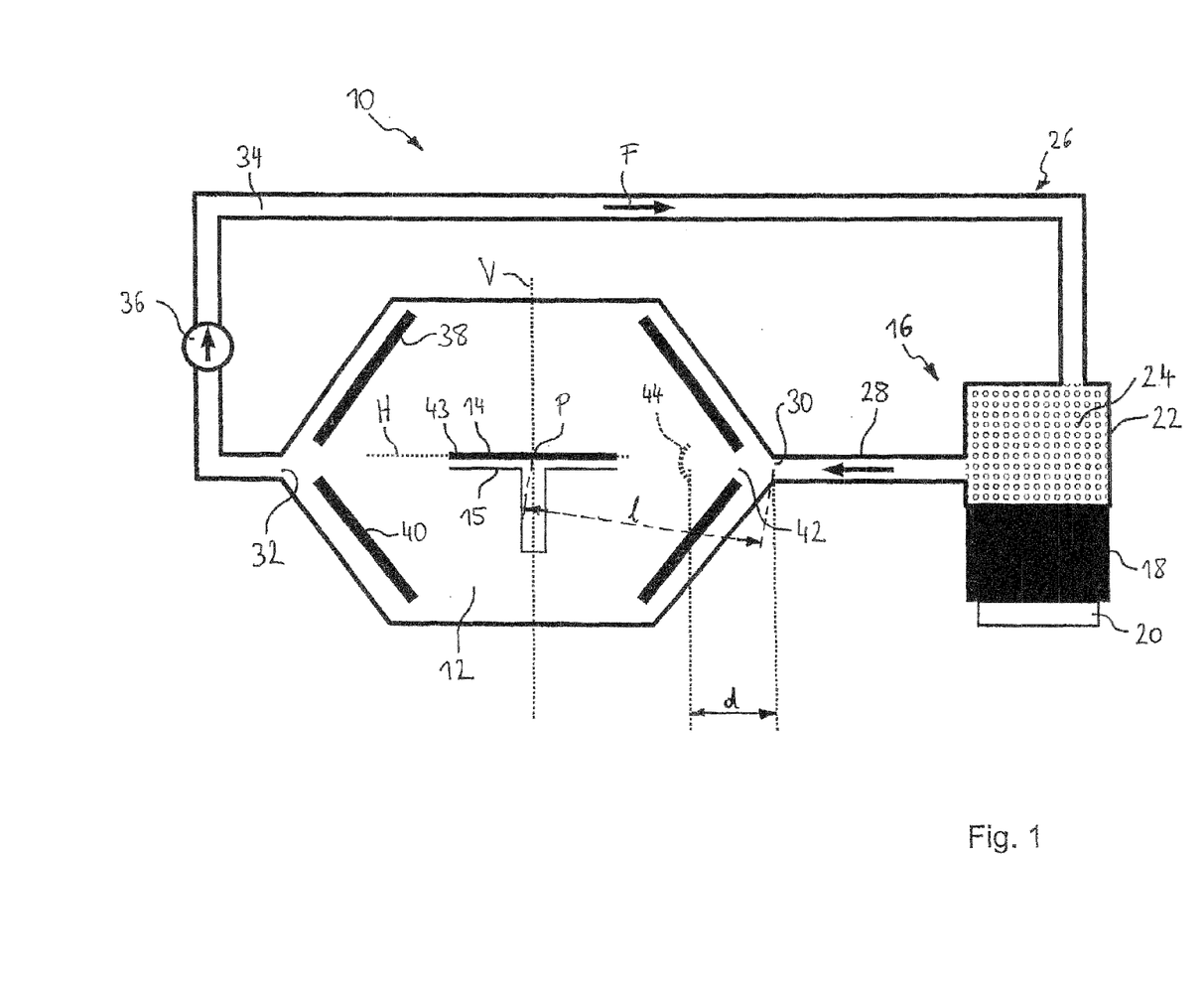
FIG. 1 shows a schematic representation of an incubator device according to a first exemplary embodiment of the invention and FIG. 2 shows a schematic representation of an incubator device according to a second exemplary embodiment of the invention.

FIG. 1 shows an incubator device of a first preferred exemplary embodiment designated 10 overall and comprising a hermetically sealable incubator chamber 12, in which a specimen 14 may be accommodated in a specimen holder 15 at a specimen position P in a horizontal plane H, in order to keep the specimen in a predetermined climate, i.e. at a predetermined temperature and predetermined humidity. The incubator chamber 12 encloses part of a microscope not shown in FIG. 1 or comprises windows for passage of observation beams for a microscope, such that the specimen 14 may be subjected to microscopic examination while being exposed to the constant climate in the incubator chamber 12.

Outside the incubator chamber an aerosol apparatus 16 is provided, which comprises a water tank 18 for accommodating water as service liquid and a piezo element 20 in contact with the water or the water tank 18. Above the water tank 18 there is located a aerosol chamber 22, which accommodates the aerosol 24 produced from the water by exciting the piezo element 20.

The aerosol apparatus 16 is part of a closed fluid circuit 26. In the direction of flow F of the fluid circuit 26 the aerosol apparatus 16 is followed by a passage channel 28, which leads to a passage opening 30, at which the passage channel 28 opens into the interior of the incubator chamber 12. The incubator chamber 12 further comprises a gas outlet opening 32, adjoined by a circulation channel 34 which connects the gas outlet opening 32 to the aerosol apparatus 16. In the circulation channel 34, just after the gas outlet opening 32, there is arranged a suction means 36, which draws gas out of the interior of the incubator chamber 12 at a predetermined velocity or flow rate. The suction means 36 acts as a fluid drive means for producing a directed flow in the circulation channel and in this way likewise brings about a directed flow of humidifying fluid from the aerosol apparatus 16 through the passage channel 28 to the passage opening 30.

The incubator chamber 12 of the exemplary embodiment shown in FIG. 1 comprises a rectangular base area in horizontal section, while in the section along the plane of the drawing in FIG. 1 it is roughly hexagonal in shape. The shape of the incubator chamber may be adapted very flexibly to the requirements of the specific application, since the configuration according to the invention of the climate control means ensures stable climate conditions even for large incubator chambers or incubator chambers with special internal geometries.

In the interior of the incubator chamber 12 two upper heating elements 38 are fitted to the internal walls of the incubator chamber 12 above the specimen plane H and two lower heating elements 40 below the specimen plane H. The heating elements 38, 40 are low temperature planar heating elements and have a particularly large radiating surface. The radiating surfaces of the heating elements 38, 40 are directed towards the specimen position P. In the present exemplary embodiment the radiating surfaces of the heating elements 38, 40 are of such magnitude that they take up a large part of the internal wall of the incubator chamber 12, in particular more than a third of the inner surface, such that a constant temperature field may be achieved.

The heating elements 38, 40 are arranged symmetrically relative to a vertical axis V through the specimen position P, such that they produce a temperature gradient extending at most substantially along the vertical axis V and thus the specimen temperature is constant over substantially the entire area of the specimen 14 in the plane H.

When the incubator device 10 is in operation, to increase the humidity in the interior of the specimen chamber 12 the piezo element 20 is switched on, which then produces an aerosol 24 from the water in the water tank 18, which aerosol collects in the aerosol chamber 22. Through operation of the suction means 36 and the resultant directed flow in the circulation channel 34, the aerosol 24 moves out of the aerosol chamber 22 through the passage channel 28 towards the passage opening 30. Because of the increased ambient temperature, the aerosol 24 starts to vaporise immediately after production thereof. Depending on specifically selected operating parameters, the vaporisation may substantially not occur until the incubator chamber 12 or may proceed as early as in the passage channel 28 or the vaporisation may optionally take place in the aerosol chamber 22 or already have been concluded there before the humidifying fluid enters the passage channel 28.

The suction means 36 is operated according to the invention at such a rate that, although a reliable, directed flow of the humidifying fluid takes place in the passage channel 28 as far as up to the passage opening 30, such that the humidifying fluid is introduced reliably into the incubator chamber 12, this directed flow is broken down substantially completely within a transition zone 42, which extends from the passage opening 30 in the passage direction into the incubator chamber 12 up to a depth d, such that outside the transition zone 42 there remain only undirected flow conditions resulting from natural convection streams, Brownian particle motion and other gas kinetic factors.

A distance between the passage opening 30 and the specimen position P is labelled 1 in FIG. 1, wherein the length of the transition zone d amounts to roughly 1/10 of the predetermined distance 1 (FIG. 1 is a schematic representation and not to scale, with size ratios possibly deviating in part markedly from the actually preferred conditions for illustrative purposes). On the basis of this distance ratio, it is ensured that a directed flow of the humidifying fluid does not itself impinge on the peripheral zones 43 of the specimen 14. For a typical incubator device the distance d may amount to for example roughly 2 cm.

In a variant of the invention illustrated in FIG. 1 by broken lines, a baffle plate 44 is arranged in the incubator chamber 12 at a distance of approx. 2 cm from the passage opening 30, such that the flow of the humidifying fluid through the passage opening 30 is directed onto the baffle plate 44. By using such a baffle plate it is in any case possible to ensure that the directed flow of the humidifying fluid at least does not reach the region of the immediate surroundings of the specimen position P. In some embodiments the velocity of the humidifying fluid may in this case also be increased (e.g. to a velocity which without the baffle plate would result in the directed flow of the humidifying fluid reaching as far as the specimen position), in order for instance to ensure more rapid or more reliable entry of the humidifying fluid into the incubator chamber 12. The baffle plate 44 then deflects the humidifying fluid in a direction which does not lead directly to the specimen position P.

Figure 2:
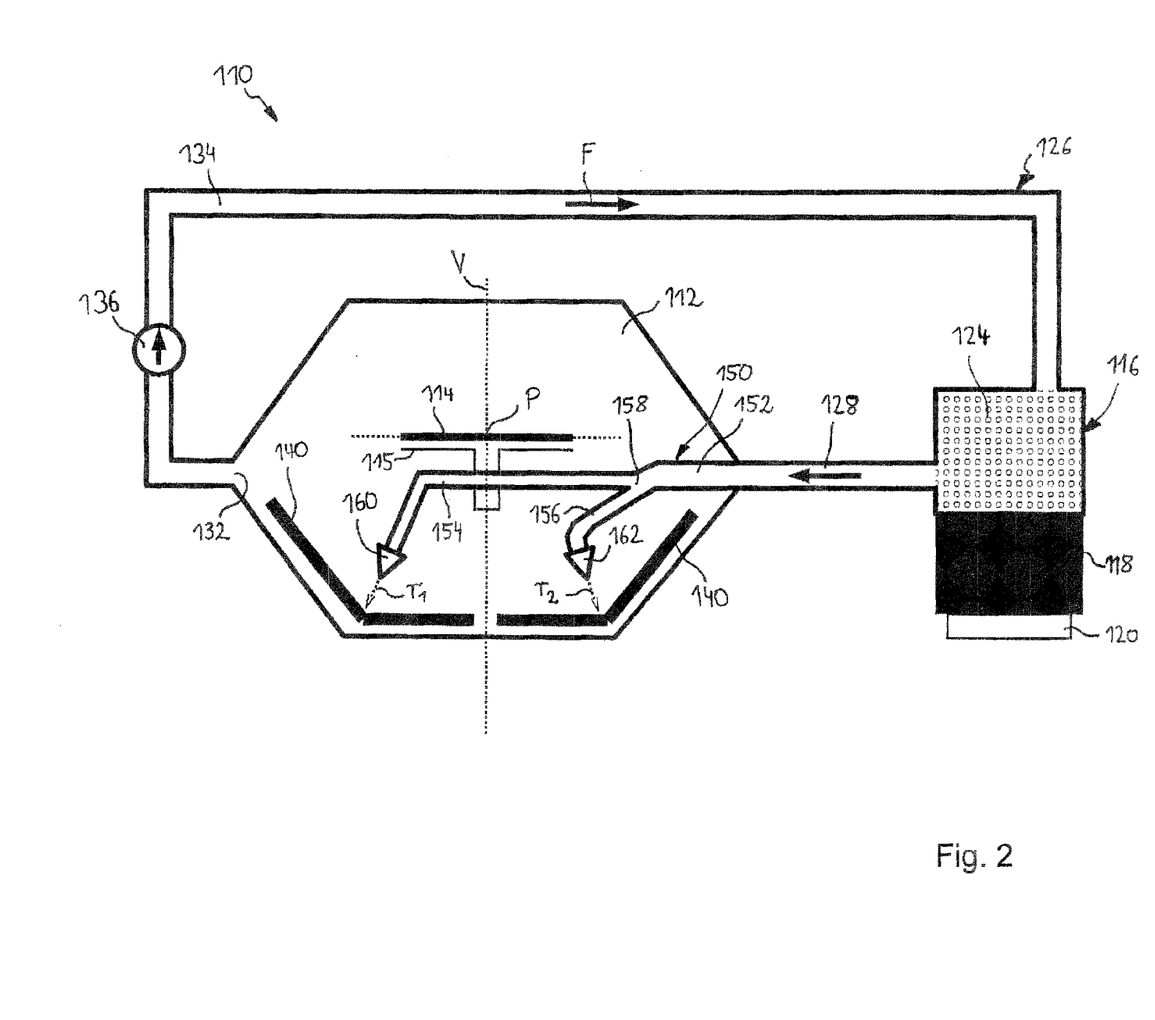

A second exemplary embodiment of the invention will be explained below with reference to FIG. 2. Features in FIG. 2 which are identical to or match features in FIG. 1 are labelled with reference signs increased by 100. Only the differences from the first embodiment will be explained below in greater detail, wherein with regard to the other features and effects explicit reference is made to the description of the first exemplary embodiment.

The incubator device 110 of the second exemplary embodiment differs from the incubator device 10 of the first exemplary embodiment particularly in that prior to entry into an incubator chamber 112 humidifying fluid 124 is guided in a fluid line 150 which is arranged in the interior of the incubator chamber 112. The fluid line 150 is branched and comprises a common feed portion 152 and a first branch portion 154 and a second branch portion 156, which branches off from the feed portion 152 at a branch point 158.

At the free end of the first branch portion 154 a first nozzle 160 is arranged and at the free end of the second branch portion 156 a second nozzle 162 is arranged. The branch portions 154 and 156 of the fluid line 150 are guided in the interior of the incubator chamber 112 such that the two nozzles 160 and 162 allow humidifying fluid to pass into the interior of the incubator chamber 112 simultaneously at different locations. The nozzles 160 and 162 each form a passage opening for the purposes of the present invention.

The nozzles 160 and 162 are designed to release humidifying fluid in a directed manner, wherein the first nozzle 160 releases humidifying fluid in a release direction $r_1$ and the second nozzle 162 releases humidifying fluid in a release direction $r_2$. As is clear from FIG. 2, the release directions $r_1$ and $r_2$ each extend in a direction away from the specimen position P, in the present case they even form an angle of roughly 180° with a direction pointing towards the specimen position P, such that the influence of the directed flow of humidifying fluid on the specimen is markedly reduced.

In addition, the release directions $r_1$ and $r_2$ are directed onto heating plates 140, which are impermeable to humidifying fluid and for the purposes of the invention form humidifying fluid deflecting faces. At these heating plates 140 the flow of the humidifying fluid is deflected to a number of sides, such that the directed flow of the humidifying fluid is further reduced drastically, since to a certain degree the flow is scattered at the heating elements 140.

Deflection of the humidifying fluid stream at the heating elements 140 has the additional advantage that the humidifying fluid does not condense at the temperature-controlled surface of the heating elements 140. This prevents individual droplets of the aerosol 124 from merging into a liquid film at the deflecting face and thus not being available for the input of humidity into the interior of the incubator chamber and instead remaining on the deflecting faces and bringing about soiling thereof.

Operation of the incubator device 110 of the second exemplary embodiment proceeds very largely in accordance with that of the first exemplary embodiment. Through the action of a suction means 136 a humidifying fluid formed from an aerosol 124 enters a passage channel 128 from an aerosol apparatus 116 and is conveyed by said passage channel into the fluid line 150. At the branch point 158 a first part of the humidifying fluid flows into the first branch portion 154, while a second part of the humidifying fluid enters the second branch portion 156. At the nozzles 160, 162 the humidifying fluid passes in each case in release directions $r_1$ and $r_2$ into the interior of the incubator chamber 112 and then impinges on a respective heating element 140. The humidifying fluid is deflected by the heating element 140, directed flow being reduced. The heating elements 140 are preferably oriented such that the reflection directions in which the humidifying fluid impinging on the heating elements 140 is deflected do not point directly towards the specimen position.

As a result of the orientation of the nozzles 160, 162 the distance to be traveled to the specimen position P is lengthened for the humidifying fluid. Deflection at the heating elements 140 brings about directional break-up or scattering of the directed flow. Furthermore, the provision of a plurality of passage openings further distributes flow of the humidifying fluid. Finally, in the second exemplary embodiment too the velocity at which the humidifying fluid enters the incubator chamber 112, i.e. the power of the suction means 136, is set to a suitable low value. All these measures contribute to reducing the directed flow of humidifying fluid at the site of the specimen P to such an extent that at the specimen position substantially only undirected flow conditions remain, for example resulting from natural convection streams, caused by operation of the heating elements, or diffusion streams. At any rate, any residual flow at the specimen site P is reduced to a level not affecting the specimen climate, such that a constant climate may be maintained over the entire specimen surface and nevertheless adjustment of desired climatic conditions at the specimen site is possible.

The invention is not restricted to the exemplary embodiment illustrated. For instance, instead of a closed fluid circuit 26, 126 it is possible to use an open system, wherein passage opening and gas outlet may be operated at the same or indeed at different flow rates or a gas outlet may be omitted completely, in order to build up a defined overpressure in the incubator chamber. In addition, although FIG. 2 just shows two lower heating elements 140, the incubator device 110 could likewise also be provided with just upper or with upper and lower heating elements.

The invention claimed is:

1. An incubator device, comprising:
   an incubator chamber;
   a specimen carrier, which is designed to accommodate a specimen and position the specimen in the interior of the incubator chamber at a specimen position;
   a heating arrangement with at least one heating element;
   a humidifier for producing a humidifying fluid; and
   a passage opening arranged between the humidifier and the interior of the incubator chamber, through which the humidifying fluid passes with directed flow into the interior of the incubator chamber in a passage flow direction;
   wherein:
   the at least one heating element is arranged inside the incubator chamber so as to directly oppose the specimen carrier and to release heat directly onto the specimen carrier;
   an active heating surface of the at least one heating element is completely uncovered in a direction towards the specimen carrier with no element intervening between the active heating surface of the at least one heating element and the specimen carrier so as to achieve homogeneous heating of the specimen substantially by thermal radiation such that a temperature of the specimen is influenced without using a fluid flow which impairs a constant nature of the climate in the incubator chamber; and
   the passage flow direction extends in a direction away from the specimen position.

2. The incubator device according to claim 1, wherein the passage opening is provided at a nozzle portion of a fluid line extending in the interior of the incubator chamber.

3. The incubator device according to claim 1, wherein the heating arrangement exhibits a substantially symmetrical structure and/or symmetrical heat release characteristic relative to a vertical axis through the specimen position.

4. The incubator device according to claim 1, wherein the at least one heating element comprises a planar heating element.

5. The incubator device according to claim 1, wherein a plurality of upper heating plates are arranged above a specimen plane and substantially symmetrically relative to a vertical axis extending through the specimen position and/or a plurality of lower heating plates are arranged below the specimen plane and substantially symmetrically relative to the vertical axis.

6. An incubation method, comprising:
accommodating a specimen in a specimen carrier in an interior of an incubator chamber at a specimen position;
operating at least one heating element;
operating a humidifier, such that it produces a humidifying fluid; and
moving the humidifying fluid to a passage opening, such that the humidifying fluid enters the interior of the incubator chamber through said passage opening in a passage flow direction with directed flow;
wherein:
the at least one heating element is arranged in the interior of the incubator chamber so as to directly oppose the specimen carrier and to release heat directly onto the specimen carrier;
an active heating surface of the at least one heating element is completely uncovered in a direction towards the specimen carrier with no element intervening between the active heating surface of the at least one heating element and the specimen carrier so as to achieve homogeneous heating of the specimen substantially by thermal radiation such that a temperature of the specimen is influenced without using a fluid flow which impairs a constant nature of the climate in the incubator chamber; and
the passage flow direction extends in a direction away from the specimen position.

7. The incubation method according to claim 6, wherein:
the specimen carrier is designed to position a specimen in the interior of the incubator chamber at a specimen position, which is at a predetermined distance from the passage opening; and
the length of a transition zone in the passage direction of the passage opening is between about 0 and about ¼, of the predetermined distance.

8. The incubator device according to claim 4, wherein the at least one heating element comprises a low temperature planar heating element.

9. The incubation method according to claim 7, wherein the length of the transition zone in the passage direction of the passage opening is between about 1/100 and about 1/10 of the predetermined distance.

10. The incubation method according to claim 6, wherein:
the specimen carrier is designed to position a specimen in the interior of the incubator chamber at a specimen position, which is at a predetermined distance from the passage opening;
and
the length of a transition zone in the passage direction of the passage opening is between about 0 cm and about 10 cm.

11. The incubation method according to claim 10, wherein the length of the transition zone in the passage direction of the passage opening is between about 1 cm and about 3 cm.

* * * * *